United States Patent [19]

Schneider et al.

[11] Patent Number: 5,386,066
[45] Date of Patent: Jan. 31, 1995

[54] CATALYST AND PROCESS FOR HYDROGENATION OF CARBOXYLIC ACID ALKYL ESTERS TO HIGHER ALCOHOLS

[75] Inventors: Michael Schneider, Ottobrunn; Karl Kochloefl, Brückmuhl/Heufeld; Gerhard Maletz, Brückmuhl, all of Germany

[73] Assignee: Sud-Chemie AG, Munich, Germany

[21] Appl. No.: 212,686

[22] Filed: Mar. 11, 1994

Related U.S. Application Data

[63] Continuation of Ser. No. 993,422, Dec. 21, 1992, abandoned.

[30] Foreign Application Priority Data

Dec. 23, 1991 [DE] Germany ............... 4142899

[51] Int. Cl.$^6$ ................. C07C 29/149; C07C 31/125; B01J 23/32
[52] U.S. Cl. .................................... 568/885; 502/324
[58] Field of Search ............................... 568/885

[56] References Cited

U.S. PATENT DOCUMENTS 3,213,145 10/1965 Field .................... 502/318 X
5,004,845 4/1991 Bradley et al. ........... 568/885

FOREIGN PATENT DOCUMENTS

| | | |
|---|---|---|
| 8767 | 3/1980 | European Pat. Off. . |
| 34338 | 8/1981 | European Pat. Off. . |
| 1408438 | 7/1965 | France . |
| 1146483 | of 0000 | Germany . |
| 2026182 | 12/1971 | Germany ............... 502/324 |
| 284167 | 11/1990 | Germany . |
| 54-053691 | 4/1979 | Japan .................... 502/324 |
| 0975134 | 11/1964 | United Kingdom ....... 568/885 |
| 2025252 | 1/1980 | United Kingdom . |
| 399097 | of 0000 | U.S.S.R. . |
| 82003854 | 11/1982 | WIPO ................. 568/885 |

*Primary Examiner*—Joseph E. Evans
*Attorney, Agent, or Firm*—Scott R. Cox

[57] ABSTRACT

A catalyst for the hydrogenation of carboxylic acid alkyl esters to higher alcohols which in the oxide form comprises a chemical composition represented by the formula $$CuZn_{0.5-2}Mn_{0.01-0.5}O_x$$

wherein x is the number of oxygen atoms needed per formula unit for electrical neutrality.

10 Claims, No Drawings

CATALYST AND PROCESS FOR HYDROGENATION OF CARBOXYLIC ACID ALKYL ESTERS TO HIGHER ALCOHOLS

This is a continuation of copending application Ser. No. 07/993,422 filed on Dec. 21, 1992 now abandoned.

BACKGROUND OF THE INVENTION

The field of art to which this invention is directed is hydrogenation of carboxylic acid alkyl esters.

Fatty alcohols, i.e., aliphatic, predominantly linear, primary alcohols with chain lengths of more than 8 carbon atoms are important intermediates in the chemical industry. They are used preferably for production of tensides, such as fatty alcohol sulfates, polyglycol ethers, or polyglycol ether sulfates. Fatty acids or fatty acid esters, such as mixtures of different chain lengths found in natural fats and oils, are important raw materials for their production. They are converted to fatty alcohols by catalytic hydrogenation under pressure.

The hydrogenation reaction is carried out as a suspension hydrogenation, as a gas-phase hydrogenation, or in the trickle phase. Sufficiently high reaction rates are attained only at pressures above 250 bar and temperatures above 200° C. As a rule, the triglycerides are transesterified by known methods before the hydrogenation with alcohols, especially with methanol, which esterifies the free fatty acids.

Hydrogenation of fatty acid methyl esters is characterized by a trend toward performing the reaction in the trickle phase.

The esters contain a more or less high residual concentration of free carboxylic acids, depending on whether or not they are subjected to purification by distillation before the hydrogenation. Choice of a suitable hydrogenation catalyst is decisively influenced by the purity of the esters used. At present, catalysts based on copper-chromium or copper-zinc have proved to be effective in industrial applications.

Aside from the hydrogenating activity, one important characteristic for evaluation of catalyst effectiveness is selectivity. When the known catalysts are used to hydrogenate fatty acid esters in the trickling phase, methane, higher hydrocarbons, and dialkyl ethers are formed. These by-products are formed at relatively high concentration, depending on the reaction temperature needed to attain a sufficiently high reaction rate. They must be removed from the reaction mixture by costly separation operations.

A process for production of a copper catalyst suitable for synthesis of methanol is known from German A-29 28 435, which is equivalent to GB 2,025,25. Along with copper oxide, it also contains zinc oxide, aluminum or chromium oxide, and manganese oxide. Use of chromium oxide is questionable, though, for environmental reasons. Aluminum oxide is not needed in catalysts for production of higher alcohols. Also, the methanol synthesis is usually carried out at pressures no greater than 20 bar.

A process for production of catalysts for synthesis of $C_2-C_5$ alcohols is known from DD A-284 167. The catalysts used are based on oxides of copper, zinc, manganese, and/or aluminum. The preferred catalysts contain about 70% copper.

The object of the present invention was to avoid the disadvantages of the known catalysts and to establish a catalyst and a process for production of alcohols by catalytic hydrogenation of carboxylic acid alkyl esters, characterized by distinctly improved selectivity.

SUMMARY OF THE INVENTION

This invention is directed to the hydrogenation of organic compounds. In one aspect, this invention pertains to catalysts used in the hydrogenation of carboxylic acid alkyl esters to higher alcohols. In another aspect, this invention relates to the process for conducting such hydrogenation reactions.

The catalyst of this invention in the oxide form has the chemical compositions which corresponds to the formula $$CuZn_{0.5-2}Mn_{0.01-0.5}O_x$$

wherein x is the number of oxygen atoms needed per formula unit for electrical neutrality.

The process of this invention comprises contacting the catalyst in reduced form with carboxylic acid alkyl esters at a temperature of about 150° C. to about 250° C. and a pressure of about 100 to about 400 bar until a saponification number of not more than 5 is obtained.

DESCRIPTION OF THE INVENTION

The catalyst of this invention in the oxide form has the chemical composition which corresponds to the formula $$CuZn_{0.5-2}Mn_{0.01-0.50}O_x$$

wherein X is the number of oxygen atoms needed per formula unit for electrical neutrality.

Preferably, the catalyst has the formula $$CuZn_{0.8-1.5}Mn_{0.05-0.2}O_x$$

wherein x has the same value as designated above.

The molded catalyst particles in the oxide form have specific pore volumes of about 0.15 to about 1.2 cm³/g and preferably about 0.2 to about 0.7 cm³/g.

The specific pore volume is determined by the mercury penetration method described by J. van Brakel et al., Powder Technology 29:1 (1981). In this method, mercury is pressed into the molded catalyst pieces at a pressure of about 2000 bar. The decrease in volume of the mercury is plotted as a function of the pressure. This gives a curve from which the pore size distribution can be determined. The mercury penetration method allows determination of volume and distribution only of pores having diameters >7.5 nm.

The catalyst in the oxide form has a BET specific surface area of about 20 to about 180m²/g. The BET specific surface area is determined by single-point $N_2$ sorption as specified in DIN 66132.

The average side crush strength of the catalyst in the oxide form is at least about 40N, preferably, at least about 60N. The transverse compressive strength is determined on a cylindrical molding having a diameter of 4.5 mm and a length of 4.5 mm, using the 4M tablet tester from the Schleuniger Company. The cylindrical molding is placed between the jaws of the instrument which exerts a pressure perpendicular to the axis of the cylinder. The rate of increase of force is 20N/sec.

The catalysts of this invention can be made by any of the known methods that guarantee sufficiently intense blending of the components. They can be made by mixing or wet milling of the copper, zinc and manganese oxides, followed by molding and, if necessary, thermal treatment. Precipitation of suitable intermediates from solutions of salts of the specified metals is a particularly preferred method. Suitable intermediates are compounds which can be converted to the oxides by thermal treatment, e.g., hydroxides, carbonates or basic carbonates. The alkali metal carbonates and bicarbonates are particularly suitable. Essentially all soluble salts, such as the halides, the sulfates, or the nitrates, are suitable raw materials.

In the hydrogenation reactions, the catalysts are used in the reduced form. The reduction is conducted in a manner which is well known in the art, such as in a hydrogen-containing gas at temperatures of about 100° C. to about 300° C. The intermediates can also be reduced directly without having first been converted to the oxides. The reduction can also be conducted in situ in the hydrogenation reactor.

The catalysts of this invention are useful in hydrogenation of unsaturated organic compounds, particularly organic compounds containing the carbonyl function, such as aldehydes, ketones, and carboxylic acids and their esters. The hydrogenation of carboxylic acid alkyl esters to the corresponding alcohols is a particularly preferred process. Examples of suitable carboxylic acid alkyl esters are those which contain about 5 to about 24 carbon atoms in the carboxylic acid portion, and 1 to about 4 carbon atoms in the alkyl ester portion.

The process using the catalysts of this invention involves contacting the catalyst in reduced form with the carboxylic acid alkyl ester at a temperature of about 150° C. to about 250° C. and a pressure of about 100 to about 400 bar until a saponification number of not more than 5 is obtained.

Preferably, the process is conducted at a temperature of about 180° C. to about 230° C. and a pressure of about 200 to about 350 bars.

EXAMPLE 1

1346 g $Cu(NO_3)_2 \cdot 3 H_2O$, 1826 g $Zn(NO_3)_2 \cdot 6 H_2O$ and 120 g $Mn(NO_3)_2 \cdot 4 H_2O$ are dissolved to a final volume of 9 liters in deionized water and heated to 60° C. This nitrate solution is pumped, over a period of 120 minutes, into a stirred precipitation tank. At the same time, a 15% sodium carbonate solution is metered in so that a pH between 6.8 and 7.0 is maintained in the precipitation tank. The temperature is kept at 60° C. The precipitate is filtered and washed by repeatedly resuspending it at 40° C. It is dried overnight at 120° C. and calcined for 3 hours at 200° C., after which the temperature is raised to 400° C. and held there for another 3 hours. The calcined product is ground and the sieve fraction less than 1 mm is tableted in a 4.5 mm×4.5 mm form.

A commercial catalyst based on a copper-chromium is used for comparison (commercial product G-99B of the applicant; metal content: Cu 36.5%; Cr 32%; Ba 2.2%; Mn 2.4%).

The catalytic effectiveness of the two catalysts for hydrogenation of fatty acid methyl esters in the trickle phase was determined as follows:

200 ml of the catalyst according to Example 1 was first reduced in a tubular reactor. The reduction gas was a mixture of hydrogen and nitrogen. The $H_2$ content of the mixture was 2%. The temperature was slowly increased from 150° C. to 200° C.

The substrate was a commercially available mixture of fatty acid methyl esters in the chain length range of $C_{12}$ to $C_{18}$. The hydrogenation was performed at 300 bar with a LHSV (liquid hourly space velocity) of 1 liter of ester mixture/liter of catalyst per hour. The saponification number was determined according to DIN 51 559 as a measure of the conversion.

The hydrogenation activity is characterized by the reaction temperature at which the desired conversion of fatty acid methyl esters is achieved. The selectivity is determined by gas chromatographic analysis of the by-products. The results are:

|  | Example 1 | Example A (comparison) |
|---|---|---|
| 1. Conversion: | | |
| Saponification number of 2 is achieved at | 220° C. | 230° C. |
| 2. By products at 230° C. reaction temperature, in moles/mole fatty alcohol | | |
| $CH_4$ | 2.5 | 5 |
| Higher hydrocarbons | 1 | 2 |
| Dimethyl ether | 0 | 3 |

Obviously, therefore, the catalyst used according to the invention is clearly superior with respect to both the hydrogenation activity and the selectivity. It must be particularly emphasized that the formation of dimethyl ether is completely suppressed.

What is claimed is:

1. A process for producing higher alcohols which comprises contacting carboxylic acid alkyl esters having about 5 to about 24 carbon atoms in the carboxylic acid portion and hydrogen with a catalyst corresponding in the oxide form to the formula $$CuZn_{0.5-2}Mn_{0.01-0.50}O_x$$

wherein x is the number of oxygen atoms needed per formula unit for electrical neutrality wherein the process is carried out at a temperature of about 150° C., to about 250° C., and a pressure of about 200 to about 400 bar to a saponification number not greater than 5.

2. The process of claim 1 wherein the temperature is about 180° to about 230° C. and the pressure is about 200 to about 350 bar.

3. The process of claim 1 wherein the catalyst corresponds to the formula $$CuZn_{0.8-1.5}Mn_{0.05-0.2}O_x.$$

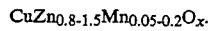

4. The process of claim 1 wherein the catalyst is in the form of moldings.

5. The process of claim 4 wherein the catalyst has a pore volume (determined by Hg porosimetry) of about 0.15 to about 1.2 $cm^3/g$.

6. The process of claim 5 wherein the catalyst has pore volume of about 0.2 to about 0.7 $cm^3/g$.

7. The process of claim 1 wherein the catalyst has an average side crush strength, measured on cylindrical moldings having a diameter of 4.5 mm and a length of 4.5 mm, of at least 40N.

8. The process of claim 7 wherein the catalyst has an average side crush strength is at least 60N.

9. The process of claim 1 wherein the catalyst has a BET specific surface area of about 20 to about 180 $m^2/g$.

10. The process of claim 9 wherein the catalyst has a BET specific surface area is about 20 to about 120 $m^2/mg$.

* * * * *